United States Patent [19]
Hatcher

[11] 4,090,000
[45] May 16, 1978

[54] METHOD FOR TREATING CELLULOSIC MATERIAL

[76] Inventor: David B. Hatcher, 8433 Katy Freeway, Houston, Tex. 77024

[21] Appl. No.: 649,705

[22] Filed: Jan. 15, 1976

[51] Int. Cl.$^2$ .......................... B27K 3/00; B44D 1/26; B44D 1/44
[52] U.S. Cl. ........................................ 427/393; 21/7; 106/15 R; 424/137; 427/397; 427/440
[58] Field of Search .......................... 21/7; 106/15 AF; 424/137; 427/440, 393, 397

[56] References Cited

U.S. PATENT DOCUMENTS

| 3,080,212 | 3/1963 | Oberley et al. | 427/440 X |
| 3,281,318 | 10/1966 | Stutz | 21/7 X |
| 3,305,298 | 2/1967 | Chapman et al. | 21/7 |
| 3,539,289 | 11/1970 | Suzuki et al. | 21/7 |
| 3,877,979 | 4/1975 | Clark | 21/7 X |
| 3,930,025 | 12/1975 | Albright et al. | 21/7 X |
| 3,945,835 | 3/1976 | Clarke et al. | 427/440 X |
| 3,957,494 | 5/1976 | Oberley | 427/440 X |

Primary Examiner—Michael R. Lusignan
Attorney, Agent, or Firm—Marshall & Yeasting

[57] ABSTRACT

A technique is provided for employing an aqueous solution to treat a cellulosic or other substrate with a water-insoluble preservative such as a polychlorophenol and the like. The treatment solution is formed of water, a soluble polychlorophenate, and a suitable acid-former which, after a predetermined delay interval sufficient to allow adequate treatment with the polychlorophenate, progressively effects in in situ precipitation of the insoluble polychlorophenol on the substrate to be protected. The extent of the delay interval, as well as the extent of the precipitation time, may be regulated as a function of temperature, the excess alkalinity of the treatment solution, and the particular acid-former employed.

5 Claims, No Drawings

METHOD FOR TREATING CELLULOSIC MATERIAL

BACKGROUND OF INVENTION

This invention relates to methods and materials for protecting permeable substances against biodegradation and the like, and more particularly relates to methods and treatment materials for impregnating wood, paper, cordage, and soil and the like with a fungicidal agent.

It is well known that wood is subject to attack by various deleterious agents such as fungi, insects, animals, etc., and it is also well known to impregnate wood and the like with various materials for the purpose of combatting such attacks. The characteristics and nature of these attacks are such that no single chemical or other material has been found to be a universal remedy, and thus it is often desirable to employ more than one type of treatment for wood and the like which is expected to be exposed to more than one type of attack. For example, it is often desired to paint the surface of wood which has also been impregnated with a preservative. Since the effects provided by one type of treatment may render the wood unsuitable for receiving another type of treatment, however, this has not always been practicable. Furthermore, recent changes in social and political attitudes with respect to the human environment have also tended to limit the use of certain treating materials previously deemed to be useful on a broader scale. Also, the cost of other treating materials has also limited their use.

Referring in particular to fungicides as a class, many different materials have been proposed and even used for this purpose. In general, however, approximately 75% of all wood which is treated with a fungicide is now impregnated with creosote, about 5% of such wood is treated with an aqueous solution of one or more salts of copper, chromium and arsenic, and about 20% is impregnated with a polychlorophenol. Creosote is both effective and long-lasting as an effective fungicidal agent. However, the popularity of creosote is attributable more to the fact that it is relatively cheap and simple to handle, since it also has a very strong and unpleasant odor which is difficult if not impossible to mask, and since wood treated with creosote is unpleasant to touch and handle. In addition, wood impregnated with creosote does not effectively receive most paints, and thus creosote-treated wood is undesirable if not unsuitable in most dwellings and the like. Furthermore, creosote is inherently foreign to wood, and thus wood tends to resist impregnation with such material.

Salts of copper, chromium and arsenic, and the like, provide an effective fungicide, as described in U.S. Pat. No. 3,080,212. These salts are quite soluble in water, and since it is far easier to impregnate wood with an aqueous solution, they are much easier to use for wood preservation purposes than creosote. Furthermore, wood treated in this manner is not inhibited against receiving paint. On the other hand, these materials are also quite expensive and, since they are water-soluble, they tend to leach out of wood which is exposed to the elements. Not only does this shorten the life of wood treated with this type of preservative, but these leached-out salts are considered a detrimental factor in the environment.

As hereinbefore stated, the third important class of wood preservatives includes the various polyhalophenols, and more particularly the polychlorophenols such as tetrachlorophenol, pentachlorophenol and, to a limited extent, trichlorophenol. Pentachlorophenol is by far the most widely used of this class of materials. Since all of these polyhalophenols have similar handling and fungicidal characteristics, however, reference will hereinafter be made to "PCP" or to polychlorophenol as denoting any polyhalophenol.

PCP-type fungicides are at least as effective as creosote insofar as their fungicidal properties are concerned, and, although they are not classified as toxic per se with respect to most insects and wildlife, wood treated with PCP tends to be avoided by many harmful insects. In addition, PCP materials are substantially cheaper than creosote. On the other hand, PCP is not water-soluble to any significant degree, and, although this is an advantage insofar as the problem of leaching is concerned, this characteristic required that PCP be employed with an organic solvent (usually No. 2 heating oil or the like). These solvents are themselves relatively expensive, which therefore significantly increases the cost of a PCP treatment operation. In addition, such solvents have the side effect of rendering the wood substantially non-paintable. Furthermore, organic solvents of this type are flammable at temperatures often experienced in wood-treating operations and must therefore be given special handling in order to safeguard personnel and property. Moreover, various environmental protection laws now require that special measures be taken to guard against escape of these solvents into uncontrolled areas, and this has added significantly to the disadvantages of using PCP fungicides rather than creosote.

It will be apparent from the foregoing that many if not most of the disadvantages attendant the use of PCP as a wood preservative may be attributed to the solvent being used, rather than to the PCP itself. As hereinbefore stated, however, PCP is substantially insoluble in water, and even when a non-flammable organic solvent has been used, the result has either been no more advantageous than when heating oil is used, or other more serious limitations have been encountered.

One attempt to avoid the problems of heating oil has involved the use of a liquified petroleum gas, such as propane or butane, as a solvent for treating wood with PCP. More particularly, the PCP is first dissolved in the propane by means of a suitable co-solvent, and the resulting mixture is then injected into the wood by means of conventional pressuring techniques. Thereafter, the propane is evaporated to deposit the PCP in the wood, with the vaporized propane being evacuated from the system.

This technique has at least one advantage over other conventonal treatment methods using PCP in that wood treated in this manner is not inhibited with respect to paintability. However, wood treated in this manner also becomes quite hard, and this renders the treatment less desirable for telephone poles since the wood cannot be penetrated as easily with climbing spikes. Moreover, vaporized propane and the like cannot effectively be reclaimed without the use of special treatment. Not only does this greatly increase costs, but the explosive character of propane in the vapor system creates an operating hazard which is even more dangerous than where a solvent such as heating oil is used.

As an alternative to the foregoing technique, it has also been proposed to use methylene chloride as a solvent for PCP to avoid the explosion hazard which is present with the use of propane and the like. This also has concurrent disadvantages, since methylene chloride is not only quite expensive in comparision with more conventional solvents, but the treatment must be maintained at either a relatively low temperature, or under pressure, or both, to prevent escape through evaporation which will further increase cost.

It has been proposed to impregnate the wood or other material with an aqueous solution of a polychlorophenate salt, and thereafter to inject an acid into the impregnated wood to precipitate the polychlorophenol in situ. A two-stage process is, of course, inherently undesirable since it requires an interim step of drying the wood after the first step to make room for the second treatment solution, and because it also requires more elaborate facilities. In this instance, however, a more serious disadvantage arises from the fact that the reactant must travel from the exterior to the interior of the wood, to achieve full permeation of the wood sought to be treated. PCP is a solid material, except when in an organic solution, and thus the PCP tends to precipitate out of solution and clog the pores of the wood at the point where the acid encounters the Na (PCP) in the wood. Since this occurs in the perimeter zones first, this effectively seals off the interior zones of the wood from the acid, and this, in turn, keeps the wood from becoming fully saturated with PCP precipitate.

These disadvantages of the prior art are overcome with the present invention, and novel methods are provided for impregnating wood with PCP at a greatly reduced cost and in a manner to the hazard of fire or explosion because of the solvent used. More particularly, wood treated by means of the present invention is fully paintable, and is fully impregnated with PCP without adversely affecting its paintability.

SUMMARY OF INVENTION

As hereinbefore indicated, the present invention has many applications besides the treatment of wood, and thus the invention is applicable to any and all uses wherein a precipitate is sought to be deposited in a selected environment over an extended period of time. More particularly, the invention includes any use or provision which contains a selected material dissolved therein and which further contains a second material or reactant which, when added to the solution, interacts to produce, on a delayed basis, a second reactant which, in turn, interacts with the first material to produce a precipitate having preselected functional properties or uses.

When considered broadly, therefore, it will be apparent that the present invention is not limited to materials having any particular solubility, nor is the invention limited to merely aqueous-type solutions. It is a feature of the invention that the seond material produces its intended reactant over a discrete time interval, rather than in an "instantaneous" manner, but the particular length of such time interval will obviously be determined by the requirements of the particular application of the invention. However, it is believed that the principles of the present invention are more easily understood with respect to its use in treating wood and the like with a PCP fungicide, since the advantages of such a use are particularly illustrative of the significant features of the invention in its basic concept. In an ideal form or example of such an application, the aforementioned solution is a treatment bath composed of an aqueous solution of a basic chemical such as a hydroxide of sodium, potassium, lithium, ammonia, nickel, calcium, magnesium, zinc, or an amine and an appropriate amount of a suitable PCP. The PCP is relatively insoluble, as heretofore explained, but it interacts in a hydroxide solution of this type to produce a water-soluble PCP salt.

Such a solution is also fungicidal in character and can therefore be used as a treatment bath. Since a PCP salt is water-soluble, however, it is subject to the disadvantage of leaching, as hereinbefore explained. Accordingly, what is desired is a means or technique for reconverting the PCP after the wood has been impregnated with the sodium PCP solution. It is well known, of course, that if an acid is added to the sodium PCP bath, the acid will interact to cause the PCP to come out of the solution as an insoluble precipitate. This reaction is instaneous, however, and what is therefore actually required is an acid-former which produces such acid in a sequential manner and only over a preselected minimum time interval. Accordingly, a particularly suitable acid-former, for these purposes, has been found to be a reactant such as ethyl acetate, methyl formate, trimethyl phosphate, ethylene chlorohydrin or the like.

THEORY OF INVENTION

There are many acid-formers which are suitable for purposes of the present invention, although commercial suitability will obviously depend upon many factors such as relative solubility, the rate at which the acid is formed, etc. The principle is illustrated, however, by an acid-former such as ethyl formate.

It is well known, of course, that an ester is produced from the reaction of an alcohol and an acid, and it is further well known that this reaction is a reversible phenomenon which tends to approach equilibrium. Accordingly, when the ester is combined with an excessive amount of water (as when it is deposited in the treatment solution), the reaction will be driven in the opposite direction to produce the acid and the alcohol, until a new equilibrium is reached. Furthermore, the rate at which this reaction occurs is a function of the rate at which the particular ester hydrolyzes, the amount of excess water in the reaction, and the temperature at which the reaction takes place. The rate at which hydrolysis occurs, for any ester in a particular series, will generally be functionally related to its molecular weight.

If the acid is removed as fast as it is produced, and if the water in the reaction continues to be excessive, then it will be apparent that equilibrium cannot be attained and that the reaction will proceed at that rate until the ester has been exhausted from the solution. In the present invention, the acid is first removed as it is produced by overcoming the excess alkalinity of the solution. After this is achieved, however, the acid then being produced will interact with the polychlorophenate salt to produce precipitation of the polychlorophenol in the wood or other substrate sought to be protected.

In a typical reaction, the pH of the treatment solution may be measured as an approximate indicator of the progress of the reaction. Thus, the pH will initially be at a maximum, due to the excess alkalinity of the solution, but will decline at a relatively rapid rate during the intial "delay" interval, as hereinbefore explained. After the excess alkalinity has been removed, however, the pH of the treatment solution will hold relatively constant, or will decline only gradually, as the polychlorophenol is precipitated out of the solution. The reason for this is that the polychlorophenol is a weaker less soluble acid than the acid being produced from the ester. The acid from the ester is removed as it is produced, by interaction with the polychlorophenate, and thus the reaction will continue until either the ester or the polychlorophenate has been exhausted from the solution.

It is usually preferable to precipitate as much polychlorophenol as is conveniently possible, and so it is usually preferable that the treatment solution be oversupplied with acid-former rather than polychlorophenate. Accordingly, in a conventional application of the present invention, exhaustion of the polychlorophenate from the solution will be indicated by an abrupt decrease in pH. In other words, the ester will continue to produce acid and alcohol irrespective of exhaustion of the polychlorophenate, and accumulation of such acid in the solution will tend to produce the relatively abrupt decrease in the pH of the treatment solution, as hereinbefore explained.

As hereinbefore stated, the circumstances relating to the particular application of the invention will often be determinative of the particular salt and acidformer to be selected. In addition, environmental parameters such as temperature, concentration and the like will affect the rate of acid production. For example, the wood sought to be treated may have been kiln-dried or steam-dried and may thus contain a considerable amount of heat when immersed in the treatment bath. Under these circumstances, the heat from the wood may have an accelerating effect on the production of acid within the wood. Also, concentration of any ingredient can be controlled over wide ranges.

As hereinbefore stated, factors such as solubility are not a factor insofar as operability of the present invention is concerned, although such factors are often important insofar as commercial practicability for specific applications may be involved. For example, it is generally recognized that, to be effectively protected from fungi, a body of wood must contain approximately 1/10 lb. of PCP or more in each cubic foot. Since the PCP is being precipitated out of the solution impregnating the wood, it is apparent that each cubic foot of the wood must be impregnated with enough PCP salt to achieve this degree of precipitation. It will further be apparent that although solubility of the PCP salt is not per se a factor insofar as achieving delayed precipitation is concerned, it is certainly a factor insofar as the amount of precipitate which will occur. If a relatively insoluble PCP salt is to be employed, it is obviously necessary to inject more solution into the same amount of wood to achieve a particular amount of precipitate, in comparison with using a PCP salt of greater solubility. Woods vary in density and therefore impregnability, however, and thus a PCP salt which is useful for some applications may not be practical for other applications.

Acid-formers will also differ with respect to acceptability for particular applications, not only with respect to relative solubility, but also with respect to the rate at which they produce acid. A certain minimum time is required to impregnate a particular body of wood, not only because of its density but also because of its size, and it is undesirable for precipitation to begin until complete impregnation has been effected. On the other hand, precipitation of PCP does not commence until the excess alkalinity of the solution has first been neutralized, and it is within the scope of this invention to selectively control this initial delay interval by selectively controlling the amount or margin of such excess alkalinity.

It is also within the scope of this invention to selectively regulate the temperature of both the wood and/or the treatment bath in order to further control both the rate of acid production and the solubility of the materials in the solution. Thus, controlling the temperature at which the reaction occurs will not only serve to accelerate or decelerate the production of acid, but can extend or narrow the duration of the initial delay interval.

Solubility is not only affected by the temperature of the solution, but may also be enhanced by the addition of co-solvents to the treatment bath. For example, various alcohols such as methyl, ethyl and isopropyl alcohol may be suitable for these purposes. Other cosolvents will include ethylene and propylene glycol, glycerine, and glycol ethers such as the methyl ether of etheylene glycol or diethylene glycol. Accordingly, use of a proper co-solvent can render suitable certain PCP salts and acid-formers normally thought to be unsuitable.

It should be noted that, as a general rule, a smaller amount of such ester or other acid-former will be required if the ester has a relatively lower molecular weight. For example, approximately 60 lbs. of methyl formate is required to release about 266.5 lbs. of PCP, whereas about 88 lbs. of ethyl acetate is required to release the same amount of PCP under similar ambient operating conditions. On the other hand, approximately 156 lbs. of isopropylpropionate is required to produce 266.5 lbs. of PCP under the same ambient operating conditions.

The rate at which acid is required to be produced is, of course, dependent primarily on specific needs. As a general rule, however, a slower rate of acid production is preferable to a faster rate, since it is preferable that the wood not only be fully impregnated but also removed from the bath before acid production is commenced to any significant degree. In fact, it is usually preferable that PCP precipitation not progress to any significant degree until the treated wood has been installed in the environment within which fungi may be expected to occur. On the other hand, it is acceptable for most purposes if the acid does not appear for 1-2 hours or so after the injection step has been completed.

The time required to treat wood by means of the present invention will not ordinarily vary to any significant extent from the time required for conventional injection-type processes. Only one treatment bath is usually required, notwithstanding that the bath is composed of both the PCP salt and the delayed acidforming agent, and injection of such a treatment solution will not require a greater period than that required by conventional injection techniques.

Although the objectives of this invention have been stated to be the production of at least 1/10 lb. of PCP within such cubic foot of wood sought to be treated, it should be clearly understood that a greater or lesser amount of PCP may be needed, depending upon conditions having nothing directly to do with the efficacy of the process. Similarly, although approximately 15-20 lbs. of solution is usually the maximum amount of liquid to be injected into each cubic foot of wood to be treated, it could be that circumstances may reasonably call for injection of as much as 60 lbs. or more of solution into each cubic foot of wood.

Although the present invention has heretofore been described with respect to its usefulness as a method or technique for protecting wood against attack by fungi, it should also be recognized that the invention has utility for any application wherein delayed precipitation of a polychlorophenol in situ is desired. For example, PCP is well known to be useful for soil treatment purposes because of its biodegradable characteristic, and it has been effectively used as a herbicide for this same reason. On the other hand, the organic solvents which have hitherto been used to provide the treatment solution are undesirable for some applications and are always relatively expensive. The techniques of the present invention effectively overcome these disadvantages of the prior art by providing a basis for using an aqueous precipitate of PCP.

Other suitable acid-formers will include organic esters such as methyl formate and the like which, when added to a solution of Na (PCP), for example, will produce formic acid also at a rate which is functionally related to the temperature of the wood and the solution, and also in a manner functionally related to the overall alkalinity of the solution (less the acidity of the wood itself). Additional suitable acid-formers include propylene chlorohydrin, ethylene chlorohydrin, and various esters of chloropropionic acid, as exemplifying a class of chlorine-containing, oxygenated compounds which, upon mixture with Na (PCP) and the like, cause hydrochloric acid to be liberated by dehydrohalogenation of such compound under operating conditions normally experienced during treatment of wood. Other acid-formers include esters formed by reacting inorganic acids with organic alcohols. For example, esters of phosphorous and sulfur-containing acids; tri-methyl phosphate, tris (hydroxyethyl) phosphate, and alkyl and aryl sulphates can be combined with ethyl, methyl and even isopropyl alcohol for these purposes.

Although solubility of a substance is important to its suitability as an acid-former, just as solubility is a factor in selection of a suitable PCP salt, it will be apparent that such solubility can also be controlled or enhanced for the reasons hereinbefore set forth. In this respect, the present invention will have applicability within a variety of different operating parameters, such as ambient temperatures of 0°–150° C., and such as injection pressures extending as high as 250 psig or even higher.

EXAMPLES OF THE INVENTION

As hereinbefore stated, as essential feature of an operable acid-former is that it produce an acid in a progressive rather than in an instantaneous manner, since if it has this capability its utility for purposes of the present invention will be clearly apparent. Following is a schedule showing how a variety of such acid-formers have performed in an aqueous solution containing pentachlorophenate.

The tests were performed with a 100 ml quantity of an aqueous solution of sodium pentachlorophenate having a concentration equivalent to 5.33% pentachlorophenol, and further being maintained at a temperature of 22° C. Each acid-former hereinafter listed was tested by adding an amount of such acid-former to the phenate solution equal to a molar ratio of 2:1 acid-former/NaPCP. The rate at which precipitation of PCP was achieved was determined as a function of the pH of the solution, the initial pH of the Na PCP solution being determined to be 12.1.

| Time After Add'n of Acid Form. | Tri-methyl Phosphate | Ethyl Formate | Methyl Formate | Diethyl Succinate | Dimethyl Succinate | Ethyl Lactate |
|---|---|---|---|---|---|---|
| 10 min. | 12.1 | 8.3 | 8.0 | 10.25 | 9.6 | 9.2 |
| 30 min. | 12.1 | 7.95 | 7.9 | 10.05 | 9.6 | 8.6 |
| 1 hr. | 11.95 | 7.95 | 7.75 | 9.6 | 8.7 | 8.5 |
| 2 hr. | 11.95 | 7.80 | 7.75 | 9.45 | 8.75 | 8.25 |
| 3 hr. | 12.05 | 7.70 | 8.00 | 9.40 | 8.70 | 8.25 |
| 4 hr. | 11.95 | 7.85 | 7.90 | 9.10 | 8.50 | 8.10 |
| 5 hr. | 11.80 | 7.70 | 7.95 | 9.10 | 8.30 | 8.25 |
| 8 hr. | 11.55 | 7.70 | 7.65 | 8.8 | 8.30 | 8.0 |
| 9 hr. | 11.25 | 7.70 | 7.55 | 8.8 | 8.30 | 7.95 |
| 10 hr. | 11.75 | 7.70 | 7.50 | 8.8 | 8.40 | 7.85 |
| 21 hr. | 10.90 | 7.50 | 7.30 | 8.8 | 8.40 | 7.60 |
| 32 hr. | 10.8 | 7.80 | 7.30 | 8.35 | 7.80 | 7.45 |
| 45 hr. | 8.5 | 7.0 | 7.0 | 7.0 | 6.5 | 6.5 |
| 164 hr. | 8.0 | 7.0 | 6.5 | 7.0 | 6.5 | 6.5 |

Other acid-formers have also been tested under the same conditions and, as indicated by the following schedule, significant differences appear only as to the rate at which pentachlorophenol is precipitated in the solution, since differences in the magnitude of the pH are largely atributable to differences in rate of hydrolysis, i.e., acid-forming, between the various materials.

| Time After Add'n of Acid Form. | Ethyl Acetate | Ethyl Propionate | Ethylene Chlorohydrin | Iso-amyl Propionate | Diethylene Glycol Diacetate | Iso-amyl Acetate |
|---|---|---|---|---|---|---|
| 10 min. | 10.1 | 10.4 | 11.2 | 12.0 | 8.9 | 11.2 |
| 30 min. | 9.7 | 9.55 | 10.05 | 11.8 | 8.4 | 10.6 |
| 1 hr. | 9.2 | 9.30 | 10.00 | 11.80 | 8.7 | 10.5 |
| 2 hr. | 9.15 | 9.30 | 10.00 | 11.35 | 8.5 | 10.1 |
| 3 hr. | 9.10 | 9.20 | 9.80 | 11.30 | 8.3 | 10.05 |
| 4 hr. | 8.9 | 9.0 | 9.50 | 10.70 | 8.35 | 9.95 |
| 5 hr. | 8.95 | 8.95 | 9.35 | 10.55 | 8.4 | 9.85 |
| 8 hr. | 8.6 | 8.8 | 9.2 | 10.50 | 8.1 | 9.85 |
| 9 hr. | 8.8 | 8.9 | 9.2 | 10.50 | 8.1 | 9.50 |
| 10 hr. | 8.65 | 9.0 | 9.2 | 10.30 | 8.1 | 9.60 |
| 21 hr. | 8.3 | 8.5 | 8.95 | 10.0 | 7.9 | 9.35 |
| 32 hr. | 8.20 | 8.3 | 8.90 | 9.9 | 7.8 | 8.90 |
| 45 hr. | 8.0 | 7.0 | 8.0 | 8.5 | 6.5 | 8.0 |
| 164 hr. | 7.5 | 7.0 | 7.5 | 8.5 | 6.0 | 8.0 |

As hereinbefore stated, the rate at which acid formation and thus precipitation of PCP is effected is clearly a function of ambient temperature. In the following example, five grams (5.0 g) of PCP was placed in a beaker with 1.501 grams of 50% sodium hydroxide solution and enough water to make 100 ml of solution. The caustic represents almost exactly the equivalent amount needed in order to dissolve the PCP. The PCP dissolved with stirring and gentle warming. After cooling to 20° C., the pH was slightly over 10.

To this solution was added 6.05 grams of ethylene chlorohydrin, representing four times the theoretical amount of ethylene chlorohydrin necessary to convert all of the sodium PCP above to PCP. After addition of the chlorohydrin, the pH of the above solution was found to be approximately 9.0. This material was then split into two equal portions, and one half was set aside at room temperature while the other was heated for 5 hours at 100° C. The results are tabulated as follows:

| 100° C. | | | 20° C. | | |
|---|---|---|---|---|---|
| Time (Hrs.) | pH | Precipit. | Time (Hrs.) | pH | Precipit. |
| 0 | 9.0 | None | 0 | 9.0 | None |
| 5 | 7.0 | Large Amt. | 5 | 9.0 | None |
| | | | 14 | 9.0 | Hazy |
| | | | 24 | 8.9 | Slight |
| | | | 120 | 8.5 | Small Amt. |
| | | | 240 | 7.0 | Substantial |

The heated portion, after cooling and standing at room temperature for another nine hours, had a pH of 7.0. A portion of the clear liquid over the precipitate from this heated portion was dropped into dilute hydrochloric acid, and no further precipitate or haziness formed, indicating that the Na PCP was substantially all converted to PCP. In contrast to the solution at 100° C., which was substantially completely reacted in 5 hours, the portion kept at room temperature required 240 hours (10 days) to arrive at substantially the same condition.

The earlier tabulation shows that enough acid was formed from trimethyl phosphate to bring the pH to 8.0 after 164 hours. In another test of trimethyl phosphate, wherein all test parameters were the same except for temperature, the solution was refluxed for a period of 5 hours. Upon conclusion, it was determined that the pH of the solution had declined to 1.0, which indicated an acid production substantially greater than that produced after 164 hours in the solution held at room temperature.

As hereinbefore stated, there is an initial "delay" interval, during which the excess alkalinity is absorbed by the evolving acid, and wherein the fungicidal solution is injected into the wood or other material sought to be treated. The actual extent of this delay interval will, of course, depend upon such factors as the temperature and amount of excess alkalinity of the solution, and also the solubility of the acid-former, as well as upon other factors such as the temperature and natural acidity of the wood being treated. However, it will depend upon the particular acid-former selected to be used, because different acid-formers will react at different rates, depending upon such factors as their molecular weight and chemical composition. Since different applications of this invention will call for different delay intervals, it will be apparent that selection of a particular acid-former will, as in the case of selection of a suitable polychlorophenate salt, be determined by the operating requirements of the particular application. Nevertheless, the substances which are suitable for these purposes may be broadly classified as follows:

Class I

Organic esters, i.e., esters which, when hydrolyzed, produce an organic acid and an alcohol. Examples of such organic esters will therefore include:
dimethyl succinate
ethyl acetate
ethyl propionate
isoamyl acetate
methyl formate
ethyl formate
diethylene glycol diacetate
ethylene lactate
diethyl succinate

Class II

Inorganic esters, i.e., esters which, when hydrolyzed, produce an inorganic acid and an alcohol. As used herein, the term "alcohol" shall mean any monohydric or polyhydric alcohol. Examples of such inorganic esters will therefore include:
bis (ethoxyethyl) sulfate
hydroxylethylbenzene sulfonate
trimethyl phosphate
tris (hydroxyethyl phosphate)
triethyl phosphate
diethyl sulfate
dimethyl phosphate

Class III

Halogen-containing organic compounds which, in the presence of an aqueous solution containing a polychlorophenate salt, react to liberate a halogenic acid by dehydrohalogenation. Examples of such compounds are:
ethylene chlorohydrin
propylene chlorohydrin
dichloropropanol
dihydroxy chloropropane
esters of chloropropionic acid (also fits Class I)
ethylene bromohydrin
benzyl chloride
allyl bromide
2, 3-dihydroxy bromopropane

Class IV

Organic acid halides which, in an aqueous solution, hydrolyze to produce both an organic acid and a halogenic acid. Examples are:
phthaloyl chloride
benzoyl chloride
benzoyl bromide

Class V

Organic acid anhydrides and imides which, in an aqueous solution, hydrolyze to produce one or more organic acids. Examples are:
maleic anhydride
phthalic anhydride
phthalimide
tetrahydro phthalic anhydride
tetrahydro phthalimide

Class VI

There are numerous instances in the chemical literature where chemicals, when treated with alkalis, disproportionate to form acids even though these materials are not of themselves derived from, nor do they under ordinary conditions yield, acids. An example of this is benzaldehyde, which under certain conditions in the presence of alkali, produces one mole of benzoic acid and one mole of benzyl alcohol. Also, formaldehyde, in the presence of strong bases, rearranges to formic acid and methanol. Consequently, formaldehyde, and paraformaldehyde which hydrolyzes to formaldehyde in water, would also be examples of the acid-formers in Class VI.

This invention is not limited in usefulness to only the polychlorophenols, since it can also be used to achieve delayed in situ precipitation of various other substances. For example, the brominated phenols (i.e., tri, tetra, or pentabromophenols) are well known as fire retardants for cellulosic materials, and for purposes of this invention can be handled in substantially the same manner as hereinbefore set forth. In fact, this generalization can extend to any phenol having a water-soluble salt and an ionization constant below that of a mineral acid (i.e., HCl and the like). In fact, any organic acid can be deposited in situ by an acid-former, where the acid-former yields a stronger or more soluble acid than the acid sought to be precipitated. In essence, therefore, this invention broadly contemplates a process wherein a relatively insoluble treatment material is precipitated within a selected environment from a solution during a discrete time interval, and preferably only after such solution has been applied to such environment. Alternatively, the present invention also contemplates a treatment solution wherein such precipitation occurs in this manner.

Nor is this invention limited in usefulness to treatment of impregnable materials, since it is well known to apply fungicides and fire retardants to merely the surfaces of objects such as wood shingles for roofs. Moreover, this is especially the case when the shingles sought to be treated are already in place as a part of a roof assembly and the like.

It is also well known that wall paint and the like is subject to attack by fungi. Accordingly, the paint may be combined with a suitable acid-former and polychlorophenate salt before being applied to the wall or other surface to be coated, whereby the paint will become progressively saturated with polychlorophenol after it has been applied to the material substrate sought to be protected.

Other variations and modifications to the present invention will readily be apparent from the foregoing recitations and examples hereinbefore set forth. Accordingly, it should be clearly understood that the steps and quantities hereinbefore recited, as well as the various salts, acid-formers and other reactants hereinbefore listed are intended as examples only and are not intended as limitations on the scope of the invention.

What is claimed is:

1. A method of treating wood with a polyhalophenol of the class consisting of polybromophenols and polychlorophenols by means of an aqueous solution, comprising the steps of preparing an aqueous solution of a water-soluble alkaline salt of the polyhalophenol, said solution containing an acid-former which undergoes a reaction in such solution to liberate an acidic substance which displaces the polyhalophenol from said salt, said reaction being on which proceeds only gradually at ordinary temperatures, impregnating wood, with said solution while said salt is still in solution, and then maintaining the wood under conditions at which said reaction proceeds to liberate a sufficient amount of said acidic substance to cause the polyhalophenol to precipitate, the proportion of said acid-former being sufficient so that said reaction causes precipitation of at least a substantial proportion of the polyhalophenol contained in said salt.

2. A method according to claim 1 wherein the aqueous solution of a water-soluble alkaline salt of a polyhalophenol also contains a sufficient excess of a base to neutralize an initial portion of the liberated acidic substance, so as to delay the precipitation of the polyhalophenol.

3. A method according to claim 1 wherein the water-soluble alkaline salt is a salt of pentachlorophenol.

4. A method according to claim 1 wherein the wood is maintained at an elevated temperature after being impregnated with the aqueous solution, to accelerate the reaction which liberates an acidic substance.

5. A method according to claim 1 wherein the molar ratio of the acid-former to the alkaline salt in the solution is greater than 1:1.